United States Patent [19]

Takago et al.

[11] Patent Number: 5,118,828

[45] Date of Patent: Jun. 2, 1992

[54] FLUORINE-CONTAINING ORGANOSILICON COMPOUND

[75] Inventors: Toshio Takago; Hirofumi Kishita; Shinichi Sato; Hitoshi Kinami, all of Annaka; Shuji Suganuma; Koichi Yamaguchi, both of Takasaki; Kenichi Fukuda; Hirokazu Yamada, both of Annaka, all of Japan

[73] Assignee: Shin-Etsu Chemical Co., Ltd., Tokyo, Japan

[21] Appl. No.: 723,317

[22] Filed: Jun. 28, 1991

[30] Foreign Application Priority Data

Jun. 29, 1990 [JP] Japan .................................. 2-171564
Jun. 29, 1990 [JP] Japan .................................. 2-171566

[51] Int. Cl.⁵ .............................................. C07F 7/08
[52] U.S. Cl. ..................................... 556/433; 556/464
[58] Field of Search ................................ 556/464, 433

[56] References Cited

U.S. PATENT DOCUMENTS 3,433,819  3/1969  Braun ............................. 556/464 X
4,447,628  5/1984  Farukawa ....................... 556/464 X
4,528,389  7/1985  Farukawa ....................... 556/464 X Primary Examiner—Paul F. Shaver
Attorney, Agent, or Firm—Oblon, Spivak, McClelland, Maier & Neustadt

[57] ABSTRACT

The fluorine-containing organosilicon compound of the present invention is represented by the following formula:

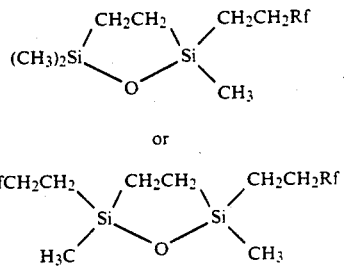

wherein Rf is a perfluoroalkyl group. This compound is quite useful as a raw material for the production of polysilethylenesiloxanes excellent in solvent resistance.

4 Claims, 3 Drawing Sheets

FLUORINE-CONTAINING ORGANOSILICON COMPOUND

BACKGROUND OF THE INVENTION

1. Field of the Invention

The present invention relates to a novel fluorine-containing organosilicon compound, and more particularly to a fluorine-containing organosilicon compound useful as a raw material for the production of fluorine-containing polysiloxanes.

2. Description of the Prior Art

It is known that polysiloxanes having fluorine atoms in the molecule are useful as a material for rubber materials excellent in solvent resistance and chemical resistance and are also useful as a material that can be used, for example, for releasing agents and water repellent and oil repellent agents.

SUMMARY OF THE INVENTION

An object of the present invention is to provide a novel fluorine-containing organosilicon compound useful as a raw material for the production of such fluorine-containing polysiloxanes.

According to the present invention, there is provided a fluorine-containing organosilicon compound represented by the following general formula [Ia] or [Ib]:

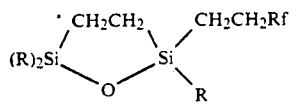

[Ia]

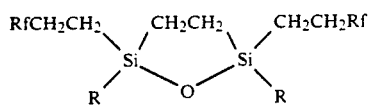

[Ib]

wherein, in the formulas [Ia] and [Ib], groups R, which may be the same or different, each represent a monovalent hydrocarbon group having 1 to 10 carbon atoms and Rf, which may be the same or different in the case of the formula [Ib], each represent a perfluoroalkyl group having 1 to 10 carbon atoms.

The fluorine-containing organosilicon compound represented by the general formula [Ia] or [Ib] is quite useful as a raw material, for example, for the production of polysilethylenesiloxanes excellent in solvent resistance.

DETAILED DESCRIPTION OF THE INVENTION

Production of Fluorine-Containing Organosilicon Compounds

Figure 1:
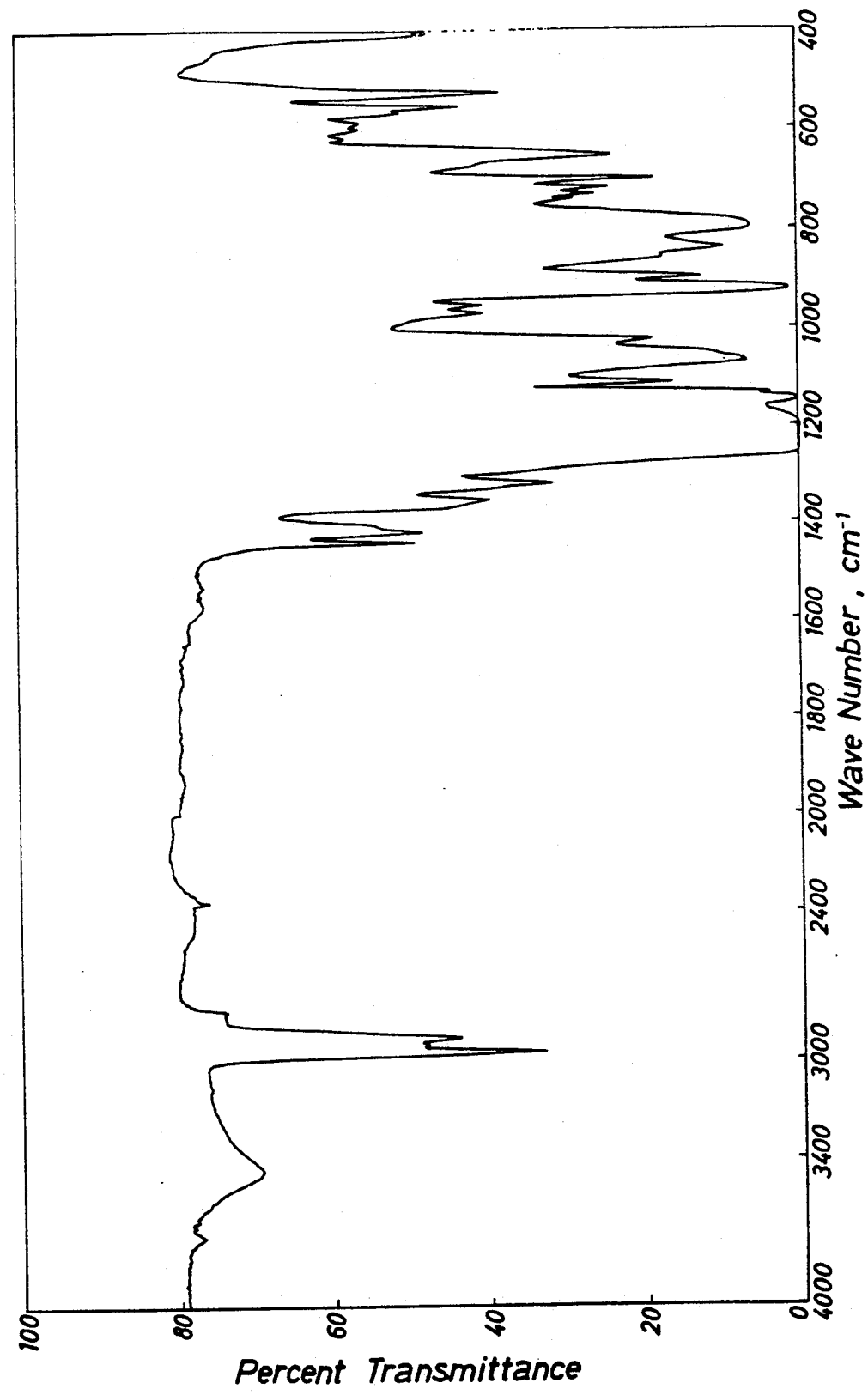
FIGS. 1 to 3 are diagrams showing infrared absorption spectra of fluorine-containing organosilicon compounds obtained in Examples 1 to 3 respectively.

The present fluorine-containing organosilicon compound represented by the above general formula [Ia] or [Ib] is produced by hydrolyzing a dichlorosilane represented by the following general formula [IIa] or [IIb]:

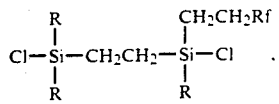

[IIa]

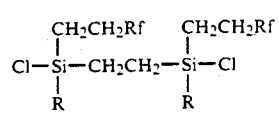

[IIb]

wherein R and Rf have the meanings defined above.

In the above general formulas [IIa] and [IIb], the groups Rf and R are groups corresponding respectively to the groups Rf and R in the above general formulas [Ia] and [Ib]. That is, the group Rf is a perfluoroalkyl group having 1 to 10 carbon atoms, for example, preferably, $-CF_3$, $-C_4F_9$, $-C_6F_{13}$, or $-C_8F_{17}$.

The group R is a monovalent hydrocarbon group having 1 to 10 carbon atoms and specifically includes a lower alkyl group having up to 8 carbon atoms such as a methyl group, an ethyl group, a propyl group, and a butyl group, a cycloalkyl group such as a cyclohexyl group, an alkenyl group such as a vinyl group, an allyl group, a propenyl group, and a butenyl group, an aryl group such as a phenyl group, a tolyl group, and a naphthyl group, and an aralkyl group such as a benzyl group and a 2-phenylethyl group. In the present invention, preferably R is an alkyl group, most preferably a methyl group.

The above hydrolyzing reaction of a dichlorosilane is carried out at a temperature in the range of 0° to 50° C., preferably 0° to 20° C. In order to obtain the fluorine-containing organosilicon compound of the general formula [Ia] or [Ib] in good yield, it is preferable to add an alkali metal oxide to the hydrolysis product followed by cracking. The alkali metal oxide used at that time includes, for example, sodium hydroxide, potassium hydroxide, and cesium hydroxide. It is desirable to use the alkali metal oxide generally in an amount of 0.01 to 2 parts by weight, particularly 0.1 to 1 part by weight, per 100 parts by weight of the hydrolysis product. The cracking reaction is carried out at a temperature in the range of 150° to 300° C., preferably 200° to 250° C.

The dichlorosilane represented by the above general formula [IIa] or [IIb] is synthesized by the addition reaction of a hydrosilane represented by the following general formula [III]:

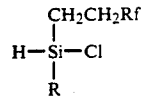

[III]

wherein R and Rf have the meanings defined above, with a vinylsilane represented by the following general formula [IVa] or [IVb]:

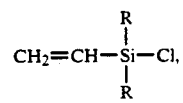

[IVa]

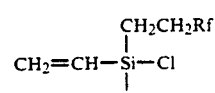

[IVb]

wherein R and Rf have the meanings defined above, in the presence of a platinum family metal catalyst. As the platinum family metal catalyst, for example, chloroplatinic acid, an alcohol-modified chloroplatinic acid (see U.S. Pat. No. 3,220,972), a complex of chloroplatinic acid with an olefin (see U.S. Pat. Nos. 3,159,601, 3,159,662, and 3,775,452), platinum black or palladium carried on a carrier such as alumina, silica, and carbon, or rhodium/olefin complex can be used. Of these catalysts, particularly complex catalysts are used preferably by dissolving the catalyst in a solvent such as alcohols, ketones, ethers, and hydrocarbons. Desirably, the platinum family metal catalyst is used generally in an amount of 0.1 to 500 ppm, particularly 0.5 to 200 ppm, in terms of the platinum family metal based on the total amount of the hydrosilane plus the vinylsilane.

Although the reaction of the hydrosilane with the vinylsilane may be carried out without any solvent, if desired, the reaction can be carried out using an inert solvent such as benzene, toluene, xylene, n-hexane, and cyclohexane. The reaction temperature is preferably in the range of 60° to 150 °C., particularly 80° to 120° C.

Fluorine-containing Organosilicon Compounds

The fluorine-containing organosilicon compound of the present invention obtained in the above manner has the molecular structure represented by the above general formula [Ia] or [Ib]. Typical examples of fluorine-containing organosilicon compound of the present invention are shown below:

Compounds of the general formula [Ia]:

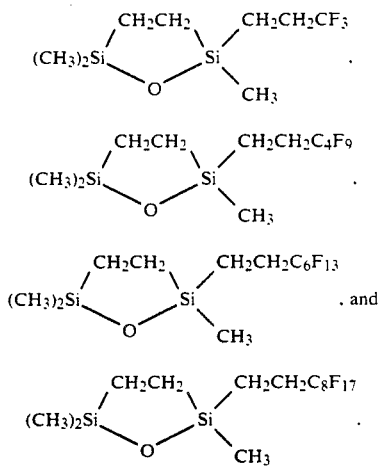

Compounds of the general formula [Ib]:

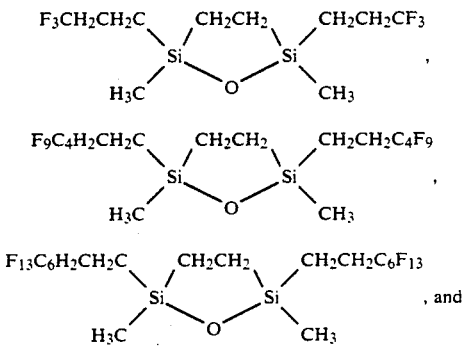

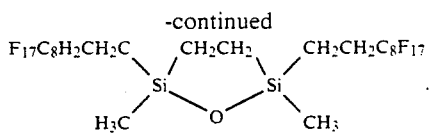

Although the fluorine-containing organosilicon compound of the present invention can be used in various applications, the fluorine-containing organosilicon compound of the present invention is particularly quite useful as a raw material for the production of polysilethylenesiloxanes excellent in solvent resistance. For example, by polymerizing the fluorine-containing organosilicon compound of the present invention, a polysilethylenesiloxane polymer having perfluoroalkyl groups in side chains can be synthesized. Since this polymer has a high fluorine content, the polymer is useful as a material for rubber materials excellent in solvent resistance and chemical resistance. Also since the polymer has a low surface energy, it is particularly useful as a material that can be used for releasing agents or the like.

EXAMPLES

Example 1

300 g of tap water was charged in a 1-l four-necked flask equipped with a condenser, a stirring rod, a thermometer, and a dropping funnel and a solution of 200 g of a dichlorosilane represented by the following formula:

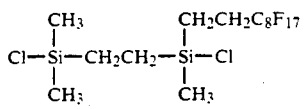

in 200 g of meta-xylene hexafluoride was added dropwise from the dropping funnel. The addition was carried out over 1 hour with the flask being cooled with ice to 10° C. or below.

Then, the lower layer of the reaction mixture was separated and was distilled under reduced pressure, thereby obtaining 110.6 g of a fraction having a boiling point of 112° to 113° C./2 mmHg (60.4% of the theoretical yield).

With respect to the fraction, the $^1$H—NMR, infrared absorption spectrum, and $^{19}$F—NMR were determined and the elemental analysis was carried out. The results are shown below:

$^1$H—NMR: in $CCl_4$, the internal standard being $CHCl_3$. δ (ppm)

0.26 (s, Si—$CH_3$, 6H)

0.29 (s, Si—$CH_3$, 3H)

0.93 (s, Si—$CH_2CH_2$—Si, 4H)

0.87 (t, Si—$CH_2$, 2H)

2.23 (t, $CF_2$—$CH_2$, 2H).

Infrared absorption spectrum: shown in FIG. 1.

C—F: 1130-1270 $cm^{-1}$

Si—O: 925 $cm^{-1}$ $^{19}$F—NMR: $CF_3COOH$ being the standard.

a: −50.04 ppm
b: −46.89 ppm
c: −45.50 ppm
d: −39.98 ppm
e: −5.61 ppm

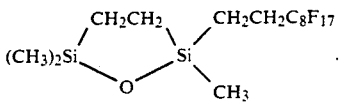

| | Elemental analysis: | | | | |
|---|---|---|---|---|---|
| | C | H | Si | F | O |
| Calculated (%) | 30.4 | 2.9 | 9.5 | 54.5 | 2.7 |
| Found (%) | 30.5 | 2.7 | 9.4 | 54.6 | 2.7 |

From the above results, the above fraction was identified

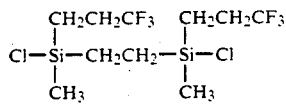

Example 2

1 l of tap water was charged in a 5-l four-necked flask equipped with a condenser, a stirring rod, a thermometer, and a dropping funnel and a solution of 871 g (2.3 mol) of a dichlorosilane represented by the following formula:

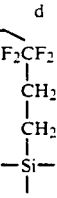

in 500 g of meta-xylene hexafluoride was added dropwise from the dropping funnel. The addition was carried out over 1 hour with the flask being cooled with ice to 10° C. or below.

Then the lower layer of the reaction mixture was separated and after the separated layer was neutralized by adding 56 g of sodium bicarbonate, the filtration was carried out and 796 g of a hydrolysis product was obtained by stripping under reduced pressure.

8 g of potassium hydroxide was added to the hydrolysis product and the mixture was heated to 160° to 250° C. under reduced pressure, thereby obtaining 598 g of a cracked fraction. When this was purified, 503 g of a fraction having a boiling point of 87° to 89° C./10 mmHg (67% of the theoretical yield) was obtained.

With respect to the fraction, the $^1$H—NMR, infrared absorption spectrum, and $^{19}$F—NMR were determined and the elemental analysis was carried out. The results are shown below:

$^1$H—NMR: in CCl$_4$, the internal standard being CHCl$_3$. δ (ppm) 0.20 (s, Si—CH$_3$, 6H) 0.80 (t, Si—CH$_2$, 4H) 0.83 (s, Si—CH$_2$CH$_2$—Si, 4H) 2.07 (t, CF$_3$—CH$_2$, 4H)

Figure 2:
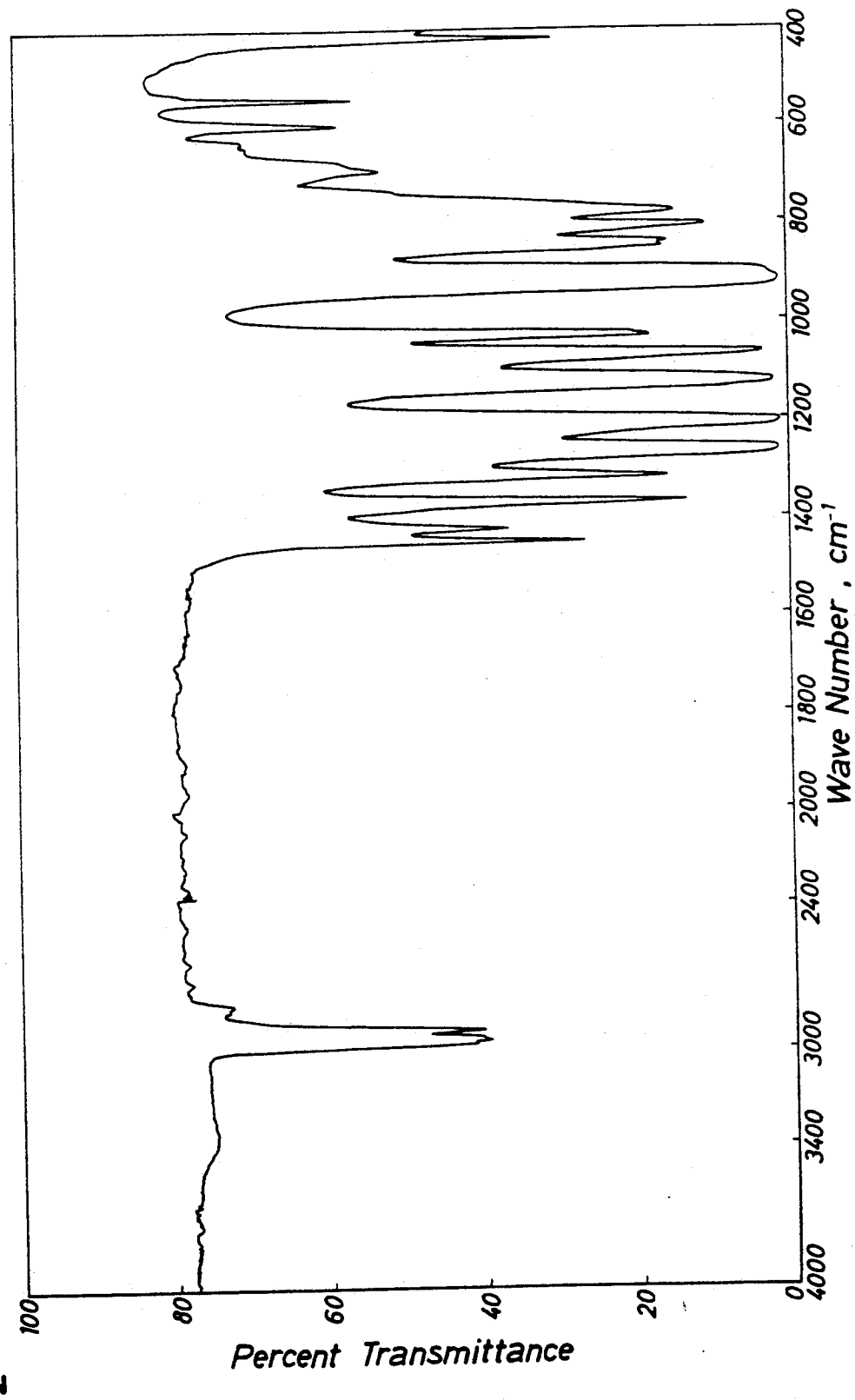

Infrared absorption spectrum: shown in FIG. 2.
C—F: 1000–1400 cm$^{-1}$
$^{19}$F—NMR: CF$_3$COOH being the standard.
CF$_3$: 8.25 ppm

| | Elemental analysis: | | | | |
|---|---|---|---|---|---|
| | C | H | Si | F | O |
| Calculated (%) | 37.0 | 5.6 | 17.3 | 35.2 | 4.9 |
| Found (%) | 37.1 | 5.5 | 17.3 | 35.1 | 4.9 |

From the above results, the above fraction was identified as

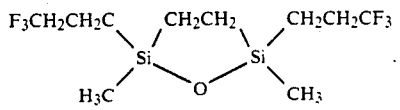

Example 3

Example 2 was repeated, except that in place of the dichlorosilane used in Example 2, 868 g of a dichlorosilane represented by the following formula:

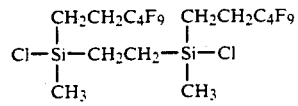

was used and the amount of the used sodium bicarbonate was 48 g, thereby obtaining 760 g of a hydrolysis product.

7.6 g of potassium hydroxide was added to the hydrolysis product and the mixture was heated to 200° to 280° C. under reduced pressure thereby obtaining 669 g of a cracked fraction. The cracked fraction was purified to produce 492 g of a fraction having a boiling point of 113° C./10 mmHg (66.5% of the theoretical yield).

With respect to the fraction, the $^1$H—NMR, infrared absorption spectrum, and $^{19}$F—NMR were determined and the elemental analysis was carried out. The results are shown below:

$^1$H—NMR: in CCl$_4$, the internal standard being CHCl$_3$. δ (ppm) 0.22 (s, Si—CH$_3$, 6H) 0.85 (s, Si—CH$_2$CH$_2$—Si, 4H) 0.87 (t, Si—CH$_2$, 4H) 2.07 (t, CF$_2$—CH$_2$, 4H).

Figure 3:
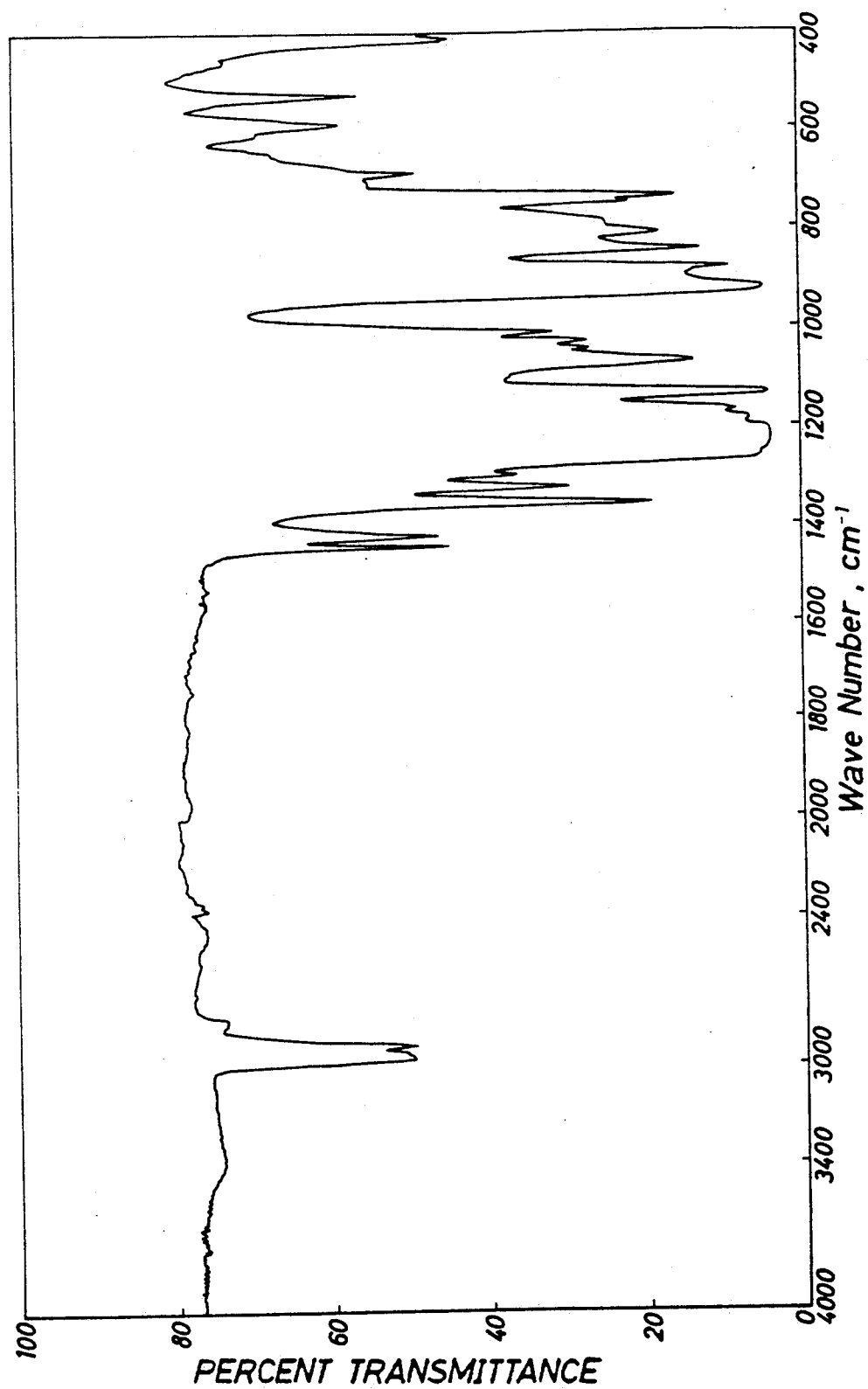

Infrared absorption spectrum: shown in FIG. 3.
C—F: 1000–1400 cm$^{-1}$
$^{19}$F—NMR: CF$_3$COOH being the standard.

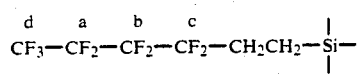

a: −52.78 ppm
b: −51.17 ppm
c: −43.11 ppm
d: −8.71 ppm

| | Elemental analysis: | | | | |
|---|---|---|---|---|---|
| | C | H | Si | F | O |
| Calculated (%) | 30.8 | 2.9 | 9.0 | 54.8 | 2.5 |
| Found (%) | 30.7 | 2.9 | 8.8 | 54.9 | 2.6 |

From the results, the above fraction was identified

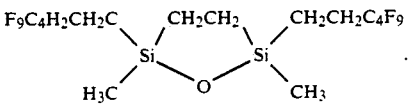

We claim:

1. A fluorine-containing organosilicon compound represented by the following general formula [Ia] or [Ib]:

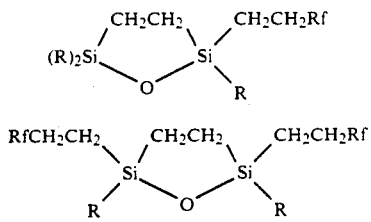

wherein, in the formulas [Ia] and [Ib], groups R, which may be the same or different, each represent a monovalent hydrocarbon group having 1 to 10 carbon atoms and Rf, which may be the same or different in the case of the formula [Ib], each represent a perfluoroalkyl group having 1 to 10 carbon atoms.

2. A fluorine-containing organosilicon compound as claimed in claim 1, wherein, in the above general formula [Ia] or [Ib], the group R is a lower alkyl group having up to 8 carbon atoms.

3. A fluorine-containing organosilicon compound as claimed in claim 2, wherein, in the above general formula [Ia] or [Ib], the group R is a methyl group.

4. A fluorine-containing organosilicon compound as claimed in claim 1, wherein, in the above general formula [Ia] or [Ib], the group Rf is selected from the group consisting of $-CF_3$, $-C_4F_9$, $-C_6F_{13}$ and $-C_8F_{17}$.

* * * * *